of Patent:

United States Patent [19]

Horodysky

[11] Patent Number: 4,557,844

[45] Date of Patent: Dec. 10, 1985

[54] AMINATED BORON- AND PHOSPHORUS-CONTAINING COMPOUNDS AND LUBRICANT OR FUEL COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 575,362

[22] Filed: Jan. 30, 1984

[51] Int. Cl.[4] .......................... C10M 1/54; C07F 9/02
[52] U.S. Cl. .................................. 252/49.9; 260/922; 252/49.6; 252/49.8
[58] Field of Search ........................ 260/922; 252/49.9

[56] References Cited

U.S. PATENT DOCUMENTS 3,450,798  6/1969  Green et al. ........................ 260/922

Primary Examiner—William R. Dixon, Jr.
Assistant Examiner—C. Johnson
Attorney, Agent, or Firm—Alexander J. McKillop; Michael G. Gilman; Van D. Harrison, Jr.

[57] ABSTRACT

Certain boron-, phosphorus- and nitrogen-containing reaction products are multifunctional additives for lubricants and liquid fuels. They have been found to be antioxidants and antifriction agents and to hinder the corrosion of copper.

24 Claims, No Drawings

AMINATED BORON- AND PHOSPHORUS-CONTAINING COMPOUNDS AND LUBRICANT OR FUEL COMPOSITIONS CONTAINING SAME

BACKGROUND OF THE INVENTION

1. Field of the Invention

This invention relates to friction reducing additives for lubricants and liquid fuels. More particularly, the invention relates to lubricant and fuel compositions to which has been added a borated phosphorus- and nitrogen-containing compound.

2. Discussion of the Prior Art

The metal surfaces of machinery or engines operating under heavy or normal loads wherein metal is under friction, undergo metal to metal contact even when being lubricated. Thus, there is always metal wear which can be excessive. Often lubricants used to protect the metal surfaces do not completely prevent wear at the points of metal to metal contact. Consequently, the performance of the machine or engine will suffer, and in aggravated cases the machine or engine may become completely inoperative from excessive wear caused the friction.

There have been many attempts to devise additive systems to improve the friction properties of a lubricant. The phosphate derivatives of the present invention are believed to be capable of overcoming some of the deficiencies of prior art additives and to provide lubricating oil compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 4,356,097 teaches an engine crankcase lubricating oil containing a dihydrocarbyl hydrocarbylphosphonate, which oil exhibits reduced friction.

U.S. Pat. No. 2,982,727 discloses lubricating oil compositions containing certain salts of oxygen-containing esters of phosphorus. The esters are phosphonates similar to those described in U.S. Pat. No. 2,758,971.

U.S. Pat. No. 4,382,035 discloses a new glycerol-3-phosphoric acid halogenalkyl ester of the formula

```
CH2—OR
|
CH—OH
|
CH2O—P(O)O(CH2)yR'
     |
     OX
``` where R, R', X and y are as defined therein. Certain diols have been disclosed as having lubricity properties when formulated into lubricants and for their water-scavaging abilities in fuels. Phosphate esters are well known as functional lubricants.

The use of boron containing compositions has also been widely reported. Borates and borate esters are disclosed in U.S. Pat. Nos. 4,370,248; 4,298,486 and 4,273,665.

Many phosphorus containing additives have found widespread use in the past. Phosphonates have been used as lubricity agents as exemplified by Papay in U.S. Pat. No. 4,356,097 in his disclosure of dihydrocarbyl hydrocarbyl phosphonate containing lubricant compositions.

Certain long chain vicinal diols are disclosed in U.S. Pat. Nos. 3,649,358 and 3,899,433.

Amines and amine borate compositions have been used as friction modifying additives, as exemplified in U.S. Pat. No. 4,328,113.

However, no art is known that teaches or suggests the phosphate ester of the present invention.

The use of the novel borates of diol-derived partial phosphate esters in lubricants provide effective multifunctional friction reducing, antioxidant, antiwear and copper passivating activity, with potential antifatigue and grease high temperature stabilizing properties.

SUMMARY OF THE INVENTION

In accordance with the invention, there are provided a product of reaction made by reacting a phosphorus oxide, preferably the pentoxide, a diol, a boron compound and a hydrocarbylamine. The invention also provides a lubricant or liquid fuel composition comprising a major proportion of a lubricant or fuel and an antifriction amount of said product of reaction. Further, lubricant and fuel compositions containing the products also have fuel consumption reducing properties when used in internal combustion engines.

DESCRIPTION OF SPECIFIC EMBODIMENTS

Because of the relatively complex nature of the reaction that occurs when, for example, phosphorus pentoxide, vicinal diols and boron compounds are interacted, no precise structure can be assigned to the product. Thus, the final product will be referred to herein, both in the specification and the claims, as the product of the specified reaction.

However, it is believed that the reaction product obtained by reacting, for example, a vicinal diol with $P_2O_5$ comprises at least some of the following compounds:

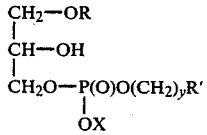  I

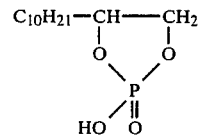

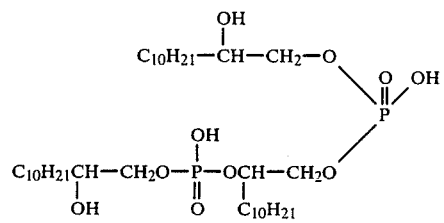  II

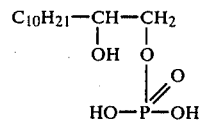  III

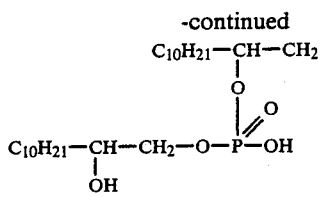

and oligomers thereof. R is defined hereinbelow. The depicted compounds react with boron compounds such as boric acid to give products in which one or more of the hydroxy groups are borated to give simple or increasingly complex molecules depending upon the number of hydroxy groups present for reaction. For example, Compound II can react with boric acid to produce a product in which 1, 2 or 3 of the hydroxy groups are reacted.

It is evident that, when the amine has been reacted with the boron-phosphate compound, the structure will be even more complex.

The products of reaction are preferably made by first reacting the diol with phosphorus pentoxide, followed by reaction of the product thus formed with a boron compound, preferably boric acid. Alternatively, they can be made by first borating the diol, and reacting this product with phosphorus pentoxide. In either case the next step involves the reaction of the boron/phosphorus intermediate with an amine, preferably an organic amine, to form the borated amine phosphate.

The hydrocarbyl diols contemplated for use in this invention are hydrocarbyl diols having vicinal hydroxy groups. They have the formula:

$$R(OH)_2$$

wherein R is a hydrocarbyl group containing 8 to 30 carbon atoms, preferably 10 to 20 carbon atoms, including mixtures thereof. At least one R is a hydrocarbyl group and can be linear or branched, saturated or unsaturated. The two hydroxy groups are preferably vicinal and near the end of the hydrocarbyl chain. The hydrocarbyl groups mentioned here and throughout this specification are preferably alkyl groups, but may also be aryl, alkaryl, aralkyl or cycloalkyl groups.

Among the diols contemplated are 1,2-decanediol, 1,2-dodecanediol, 1,2-tetradecanediol, 1,2-pentadecanediol, 1,2-hexadecanediol, 1,2-heptadecanediol, 1,2-octadecanediol, 1,2-eicosanediol, 1,2-triacontanediol, mixed 1,2-$C_{15}$-$C_{18}$ alkanediols, and mixtures of all such diols, including mixtures of similar diols. Mixtures are often preferred. Included also are diols made by the epoxidation and hydrolysis of olefins such as propylene trimer, butylene trimer, butylene tetramer and the like.

The preferred vicinal diols can be synthesized using several methods known to the art. One such method, described in an article in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat. No. 2,411,762, U.S. Pat. No. 2,457,329 and U.S. Pat. No. 2,455,892. These are incorporated herein by reference.

The diols can also be prepared via catalytic epoxidation of an appropriate olefin, followed by hydrolysis.

As disclosed hereinabove, the diols contain 10 to 30 carbon atoms. This range is preferred because the final products made with such diols appear to have significantly more friction reducing properties. That is to say, where the number of the carbon atoms in the diol have less than 10 carbon atoms or more than 20, solubility constraints or other adverse physical effects become significant and the friction properties rapidly diminish. The more preferred are diols having $C_{14}$ to $C_{18}$ hydrocarbyl groups and mixtures thereof in which solubility, frictional characteristics and other properties appear to be maximized.

Other additives, such as detergents, dispersants, antioxidants, antiwear agents, extreme pressure additives, pour depressants, antirust additives and the like may be present in the composition. These may include metal phenates and sulfonates, (such as calcium and barium phenates and sulfonates), succinimides, zinc dialkyl or diaryl dithiophosphates, polymers, calcium- and magnesium-containing additives and the like.

The useful boron compounds include boric oxide and the metaborates, as well as other boron compounds of the formula $$(R^IO)_xB(OH)_y \qquad \text{I}$$

wherein $R^I$ is a $C_1$ to $C_6$ alkyl group and x and y are 0 to 3, the sum thereof being 3. This formula includes boric acid and the alkyl borates. The latter include the mono-, di- and tri-methyl, -ethyl, -propyl, -butyl, -pentyl and -hexyl borates.

In both of the reaction schemes mentioned above, the temperature of reaction of the diol with boron is from about 80° C. to about 260° C., preferably from about 100° C. to about 160° C. and for reaction thereof with phosphorus pentoxide the temperature of reaction is from about 40° C. to about 180° C., preferably about 60° C. to about 100° C. Reaction times will vary from 1 hour to 20 hours or more.

The nitrogenous compounds that can be used include compounds of the formulae $$R^2R^3R^4N$$

and

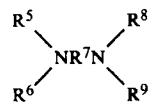

wherein $R^2$ is a $C_6$ to $C_{30}$ hydrocarbyl group, $R^3$ and $R^4$ are hydrogen or a $C_1$ to $C_{20}$ hydrocarbyl group, $R^5$ is a $C_{12}$ to $C_{20}$ hydrocarbyl group, $R^7$ is a $C_1$ to $C_4$ alkylene group and each of $R^6$, $R^8$ and $R^9$ is selected from hydrogen or a $C_1$ to $C_{20}$ hydrocarbyl group, preferably hydrogen. They include hexylamine, octylamine, decylamine, tetradecylamine, octadecylamine, eicosylamine, triacontylamine and the secondary and tertiary counterparts. They also include oleylamine, cocoamine, tallowamine, soyamine, the t-alkylamines such as t-butylamine, diamines such as N-dodecyl-1,2-ethylenediamine, N-oleyl-1,2-ethylenediamine, N-coco-1,2-ethylenediamine, N-soyl-1,2-ethylenediamine, N-tallowyl-1,2-ethylenediamine,. N-dodecyl-1,3-propylenediamine, N-oleyl-1,3-propylenediamine, N-coco-1,3-propylenediamine, N-soyl-1,3-propylenediamine, N-tallowyl-1,3- propylenediamine and the cyclic and aromatic amine counterparts of all of the novel amines.

The reaction with amines is carried out at from about 20° C. to about 120° C., preferably about 40° C. to about 80° C. The time of reaction will range from about 1 to about 10 hours or more.

In the first reaction mentioned the diol is reacted with phosphorus pentoxide so that from about 5% to about 95% of the hydroxy functions are reacted. The resulting phosphate is then reacted with boron compound to react from about 5% to 100% of the unphosphated hydroxy groups. Up to a 50% excess of boron compound may be used when complete boration is desired. The amine content can be varied, but as a minimum sufficient amine should be charged to neutralize the acidity due to the acid phosphate groups. More amine than required to neutralize the acid phosphate groups can be used. Excess amine may then interact with the boron moieties.

The alternative reaction is carried out by reacting the diol with boron compound so that about 5% to about 95% of the hydroxy groups are borated. The borated product is then reacted with enough phosphorus pentoxide to react with from about 5% to 100% of the unborated diol hydroxy groups.

A solvent is desirable in some cases where strongly exothermic reaction occurs and generally useful for the azeotropic removal of the water formed during the condensation reaction. Where a solvent is used, it should be one in which the products are soluble and which can be relatively easily removed. Examples of some solvents that may be useful in the various reactions are hydrocarbon solvents, such as toluene, benzene, xylene, cyclohexane, hexane and the like.

Atmospheric pressure is preferred, but reduced pressure is often desirable.

The compounds of the invention are used with lubricating oils or greases to the extent of from about 0.1% to about 10% by weight of the total composition, and with fuels to the extent of from about 5 lbs. to about 250 lbs. per 1000 bbls. of fuel. Furthermore, other additives, such as detergents, antioxidants, antiwear agents and the like may be present. These can include one or more of the same additives mentioned above in connection with lubricant compositions.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodecene, etc. These vicinal diols are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali metal and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils. Often preferred are thickeners containing at least 1-2% of a lithium 12-hydroxystearate soap derived from 12-hydroxystearic acids, esters or glycerides.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons.

Having described the invention in general aspects, the following Examples are offered as specific illustrations. Parts are by weight.

EXAMPLE 1

Partial Acid Phosphate of 1,2-Mixed Pentadecanediol-Octadecanediol

Approximately 480 g of 1,2-mixed pentadecanediol-octadecanediol (obtained as Vikol 158 from Viking Chemical Co. and containing approximately 28% 1,2-pentadecanediol, 28% 1,2-hexadecanediol, 28% 1,2-heptadecanediol and 16% 1,2-octadecanediol) and 200 g of hexane were charged to a 2 liter reactor equipped with agitator and condenser. The contents were warmed to about 60° C. and 70 g of phosphorus pentoxide was slowly added over a period of 2 hours while maintaining a temperature of 60°–65° C. The temperature was held at 60° C. for 1 hour and raised to 100° C. for 3 hours. The solvent was removed by distillation.

EXAMPLE 2

Partially Acid Phosphate of 1,2-Mixed Pentadecanediol-Octadecanediol Partially Borated Approximately 135 g of the product of Example 1, 75 g of toluene and 8.5 g of boric acid were charged to a reactor equipped with heater, agitator, Dean-Stark tube with condenser and provision for blanketing vapor space with nitrogen. The reactants were heated to 120° C. and held until water formation as a result of azeotropic distillation ceased. The solvent was removed by vacuum distillation at 120° C.

EXAMPLE 3

Oleylamine Salt of Borated Acid Phosphate of 1,2-Mixed Pentadecanediol-Octadecanediol Approximately 29 g of the product of Example 2 and 27 g of oleylamine (obtained as Armeen O from Armak Chemical Co.) were reacted with agitation at about 80° C. for about ½ hours.

EXAMPLE 4

Mixed t-Alkylamine Salt of Borated Acid Phosphate of 1,2-Mixed-Pentadecanediol-Octadecanediol Approximately 29 g of the product of Example 2 and 21 g of primary aliphatic amines in the $C_{12}$ to $C_{14}$ range having the following grouping

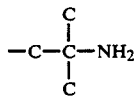

(obtained as Primene 81R from Rohm and Haas Co.) were reacted with agitation at about 80° C. for about ½ hour.

EXAMPLE 5

Partially Acid Phosphate of 1,2-Mixed Pentadecanediol-Octadecanediol

Approximately 270 g of the product of Example 1, 100 g of toluene and 11 g of boric acid were charged to a reactor equipped as generally described in Example 2. The reactants were heated up to 120° C. and held for 4 hours until water evolution as a result of azeotropic distillation ceased. The solvent was removed by vacuum distillation at 120° C.

EXAMPLE 6

Oleylamine Salt of Borated Acid Phoisphate of 1,2-Mixed Pentadecanediol-Octadecanediol Approximately 29 g of the product of Example 5 and 27 g of oleylamine (obtained commercially as Armeen O from Armak Chemical Co.,) were reacted with agitation at about 80° C. for about ½ hour.

EXAMPLE 7

N-Oleyl-1,3-Propylenediamine Salt of Borated Acid Phosphate of 1,2-Mixed Pentadecanediol-Octadecanediol Approximately 29 g of the product of Example 5 and 18 g of N-oleyl-1,3-propylenediamine (commercially obtained as Duomeen O from Armak Chemical Co.) were reacted with agitation at about 80° C. for about ½ hour.

EXAMPLE 8

Mixed t-Alkylamine Salt of Borated Acid Phosphate of 1,2-Mixed-Pentadecanediol-Octadecanediol Approximately 29 g of the product of Example 5 and 10 g of Primene 81R primary amines described in Example 4 were reacted with agitation at about 80° C. for about ½ hour.

EVALUATION OF PRODUCTS

The phosphorus esters of hydrocarbyl diols were blended into fully formulated 5W-30 synthetic lubricating oil or a fully formulated 10W-40 mineral lubricating oil and evaluated using the Low Viscosity Friction Apparatus Test. The formulations included polymeric dispersants, metallic phenates and sulfonates, zinc dithiophosphates and polymeric viscosity index improving additives.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.²). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches. The results obtained are shown in Tables 1 and 2. As shown in Table 1 1% of the product of Example 3 in a synthetic oil reduced the coefficient of friction by 52% at the lower speed. Table 2 shows that at the same concentration in mineral oil the product of Example 7 gave a 38% reduction in coefficient of friction at the lower speed.

TABLE 1

Friction Test Results Using The Low Velocity Friction Apparatus

| | Additive Conc. in Base Fluid Wt % | % Reduction In Coefficient Of Friction @ | |
|---|---|---|---|
| | | 5 Ft/Min | 30 Ft/Min |
| Base Oil A (fully formulated mineral oil based automotive engine oil containing detergent/dispersant/inhibitor performance package SAE 10w-40 | — | 0 | 0 |
| Example 2 Plus Base Oil A | 1 | 27 | 18 |
| Example 3 Plus Base Oil A | 2 | 48 | 38 |
| | 1 | 52 | 46 |
| Example 4 Plus Base Oil A | 2 | 22 | 20 |
| Example 6 Plus Base Oil A | 2 | 38 | 28 |
| Example 7 Plus Base Oil A | 2 | 34 | 26 |
| | 1 | 32 | 20 |
| Example 8 Plus Base Oil A | 2 | 28 | 21 |

TABLE 2

Friction Test Results Using The Low Velocity Friction Apparatus

| | Additive Conc. in Base Fluid Wt % | % Reduction In Coefficient Of Friction @ | |
|---|---|---|---|
| | | 5 Ft/Min | 30 Ft/Min |
| Base Oil B (fully formulated synthetic automotive engine oil containing detergent/dispersant inhibitor performance package SAE 5W-30 | — | 0 | 0 |
| Example 3 Plus Base Oil B | 2 | 43 | 40 |
| | 1 | 26 | 24 |
| Example 4 Plus Base Oil B | 2 | 34 | 33 |
| | 1 | 24 | 16 |
| Example 6 Plus Base Oil B | 2 | 38 | 34 |
| Example 7 Plus Base Oil B | 2 | 41 | 36 |
| | 1 | 38 | 26 |
| Example 8 Plus Base Oil B | 2 | 31 | 35 | t-Alkylamine salts of borated acid phosphate of 1,2-mized $C_{15}$-$C_{18}$ alkanediols were blended intdo 200" solvent paraffinic neutral lubricating oil and tested for oxidative stability using the Catalytic Oxidation Test. The test is run by bubbling air through the composition at a rate of about 5 liters per hour at 325° F. and for 40 hours. Present in the composition are samples of iron, copper, aluminum and lead, metals used in engine constructions. Results are summarized in Table 3. As shown by the control 1 in viscosity increase and control of the acidity increase, the high temperature oxidative stability of these additives is good.

TABLE 3

Catalytic Oxidation Test 325° F., 40 Hours

| | Additive Conc. Wt. % | % Increase in Viscosity of Oxidized Oil Using KV @ 100° F. | Neut. Number |
|---|---|---|---|
| Base Oil, 200" solvent paraffinic Neutral Lubricating Oil | — | 67 | 3.62 |
| Example 4 t-Alkylamine salt of borated acid phosphate of 1,2-mixed $C_{15-18}$ alkanediols | 0.5 | 11 | 1.8 |
| Example 8 t-Alkylamine salt of borated acid phosphate of 1,2-mixed $C_{15-18}$ alkanediols | 0.5 | 12 | 1.72 |

COPPER CORROSION TEST

Copper strip corrosivity properties of the additives were evaluated using ASTM D130-80 run at 250° F. for 3 hours as shown in Table 4.

TABLE 4

Copper Strip Corrosivity D130-80 250° F., 3 Hours

| | Conc. of Additive % | Rating |
|---|---|---|
| Example 4 Plus Oil | 0.5 | 1A |
| Example 8 Plus Oil | 0.5 | 1A |

The results clearly show the products of this invention to be stable and non-corrosive to copper at elevated temperature. The oil used was a 200 second solvent paraffinic neutral mineral oil.

We claim:

1. A product of reaction made by reacting phosphorus pentoxide, a vicinal diol, of the formula R(OH)$_2$ wherein R is a hydrocarbyl group containing 8 to 30 carbon atoms, a boron compound selected from the group consisting of boric oxide, a metaborate or boron compounds having the formula $$(R^1O)_xB(OH)_y$$

wherein $R^1$ is a $C_1$ to $C_6$ alkyl group and x and y are each 0 to 3, their sum being 3, and a hydrocarbylamine having one of the following formulae:

$$R^2R^3R^4N$$

and

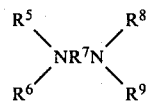

wherein $R^2$ is a $C_2$ to $C_{30}$ hydrocarbyl group, $R^3$ and $R^4$ are hydrogen or a $C_1$ to $C_{20}$ hydrocarbyl group, $R^5$ is a $C_{12}$ to $C_{20}$ hydrocarbyl group, $R^7$ is a $C_1$ to $C_4$ alkylene group and each of $R^6$, $R^8$ and $R^9$ is selected from hydrogen or a $C_1$ to $C_{20}$ hydrocarbyl group.

2. The product of claim 1 wherein the hydrocarbyl group is an alkyl, aryl, aralkyl or cycloalkyl group.

3. The product of claim 1 wherein the diol is 1,2-decanediol, 1,2-dodecandeiol, 1,2-tetradecanediol, 1,2-pentadecanediol, 1,2-hexadecanediol, 1,2-heptadecanediol, 1,2-octadecanediol, 1,2-eicosanediol, 1,2-triacontanediol, mixed $C_{15}$ to $C_{18}$ alkanediols or mixtures of any of these.

4. The product of claim 1 wherein the boron compound is boric acid, mono-, di- or trimethyl borate; mono-, di- or triethyl borate; mono-, di- or tripropyl borate; mono-, di- or tributyl borate; mono-, di-, or tripentyl borate; or mono-, di- or trihexyl borate.

5. The product of claim 4 wherein the boron compound is boric acid.

6. The product of claim 1 wherein the hydrocarbylamine is hexylamine, octylamine, decylamine, tetradecylamine, octadecylamine, eicoxylamine, triacontylamine, the secondary and tertiary counterparts thereof, oleylamine, cocoamine, tallowamine, soyamine, t-butylamine, N-dodecyl-1,2-ethylenediamine, N-oleyl-1,2-ethylenediamine, N-coco-1,2-ethylenediamine, N-soyl-1,2-ethylenediamine, N-tallowyl-1,2-ethylenediamine, N-dodecyl-1,3-propylenediamine, N-oleyl-1,3-propylenediamine, N-coco-1,3-propylenediamine, N-soyl-1,3-propylenediamine or N-tallowyl-1,3-propylenediamine.

7. The product of claim 1 wherein the diol is 1,2-mixed pentadecanediol-octadecanediol, the phosphorus oxide is phosphorus pentoxide, the boron compound is boric acid and the hydrocarbylamine is oleylamine.

8. The product of claim 1 wherein the diol is 1,2-mixed pentadecanediol-octadecanediol, the phosphorus oxide is phosphorus pentoxide, the boron compound is boric acid and the hydrocarbylamine is a mixed $C_{12}$ to $C_{14}$ t-alkylamine.

9. The product of claim 1 wherein the diol is 1,2-mixed pentadecanediol-octadecanediol, the phosphorus oxide is phosphorus pentoxide, the boron compound is boric acid and the hydrocarbylamine is N-oleyl-1,3-propylenediamine.

10. A lubricant composition comprising a major proportion of a lubricant and between about 0.1 and about 10% by weight of the total composition of a product of reaction made by reacting phosphorus pentoxide, a vicinal diol, of the formula (R(OH)$_2$ wherein R is a hydrocarbyl group containing 8 to 30 carbon atoms, a boron compound selected from the group consisting of boric oxide, a metaborate or a boron compound having the formula $(R^1O)_xB(OH)_y$ wherein $R^1$ is a $C_1$ to $C_6$ alkyl group and x and y are each 0 to 3, their sum being 3, and a hydrocarbylamine having one of the following formulae:

$R^2R^3R^4N$ and

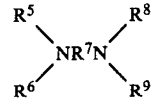

wherein $R^2$ is a $C_2$ to $C_{30}$ hydrocarbyl group, $R^3$ and $R^4$ are hydrogen or a $C_1$ to $C_{20}$ hydrocarbyl group, $R^5$ is a $C_{12}$ to $C_{20}$ hydrocarbyl group, $R^7$ is a $C_1$ to $C_4$ alkylene group and each of $R^6$, $R^8$ and $R^9$ is selected from hydrogen or a $C_1$ to $C_{20}$ hydrocarbyl group.

11. The composition of claim 10 wherein the hydrocarbyl group is an alkyl, aryl, aralkyl or cycloalkyl group.

12. The composition of claim 10 wherein the diol is 1,2-decanediol, 1,2-dodecandeiol, 1,2-tetradecanediol, 1,2-pentadecanediol, 1,2-hexadecanediol, 1,2-heptadecanediol, 1,2-octadecanediol, 1,2-eicosanediol, 1,2-triacontanediol, mixed $C_{15}$ to $C_{18}$ alkanediols or mixtures of any of these.

13. The composition of claim 10 wherein the boron compound is boric acid, mono-, di- or trimethyl borate; mono-, di- or triethyl borate; mono-, di- or tripropyl borate; mono-, di- or tributyl borate; mono-, di-, or tripentyl borate; or mono-, di- or trihexyl borate.

14. The composition of claim 7 wherein the boron compound is boric acid.

15. The composition of claim 10 wherein hydrocarbylamine is hexylamine, octylamine, decylamine, tetradecylamine, octadecylamine, eicoxylamine, triacontylamine, the secondary and tertiary counterparts thereof, oleylamine, cocoamine, tallowamine, soyamine, t-butylamine, N-dodecyl-1,2-ethylenediamine, N-oleyl-1,2-ethylenediamine, N-coco-1,2-ethylenediamine, N-soyl-1,2-ethylenediamine, N-tallowyl-1,2-ethylenediamine, N-dodecyl-1,3-propylenediamine, N-oleyl-1,3-propylenediamine, N-coco-1,3-propylenediamine, N-soyl-1,3-propylenediamine or N-tallowyl-1,3-propylenediamine.

16. The composition of claim 10 wherein the diol is 1,2-mixed pentadecanediol-octadecanediol, the phosphorus oxide is phosphorus pentoxide, the boron compound is boric acid and the hydrocarbylamine is oleylamine.

17. The composition of claim 10 wherein the diol is 1,2-mixed pentadecanediol-octadecanediol, the phosphorus oxide is phosphorus pentoxide, the boron compound is boric acid and the hydrocarbylamine is a mixed $C_{12}$ to $C_{14}$ t-alkylamine.

18. The composition of claim 10 wherein the diol is 1,2-mixed pentadecanediol-octadecanediol, the phosphorus oxide is phosphorus pentoxide, the boron compound is boric acid and the hydrocarbylamine is N-oleyl-1,3-propylenediamine.

19. The composition of claim 10 wherein the lubricant is (1) a mineral oil, (2) a synthetic oil or a mixture of synthetic oils, (3) a mixture of (1) and (2) or (4) a grease of (1), (2) or (3).

20. The composition of claim 19 wherein the lubricant is a mineral oil.

21. The composition of claim 19 wherein the lubricant is a synthetic oil or mixture of synthetic oils.

22. The composition of claim 19 wherein the lubricant is a grease.

23. The composition of claim 10 additionally containing one or more of a member selected from the group consisting of a polymeric dispersant, metallic phenate, a metallic sulfonate, a zinc dithiophosphate and a polymeric viscosity index improver.

24. A method of reducing fuel consumption in an internal combustion engine which comprises (1) lubricating said engine with a lubricant composition comprising a major proportion of a lubricating oil and a fuel consumption reducing amount of a product of reaction made by reacting a phosphorus pentoxide, a vicinal diol of the formula R(OH)$_2$ wherein R is a hydrocarbyl group containing 8 to 30 carbon atoms, a boron compound selected from the groups consisting of boric oxide, a metaborate or boron compounds having the formula $$(R^1O)_xB(OH)_y$$

wherein $R^1$ is a $C_1$ to $C_6$ alkyl group and x and y are each 0 to 3, their sum being 3, and a hydrocarbylamine.

* * * * *